United States Patent [19]

Cramer et al.

[11] 4,335,735

[45] Jun. 22, 1982

[54] AUTOMATIC DILUTER/DEMAND OXYGEN REGULATOR ADAPTED FOR CHEMICAL OR BIOLOGICAL USE

[75] Inventors: Robert L. Cramer, Davenport, Iowa; Roy L. Henneberger, Madison, Wis.

[73] Assignee: The Bendix Corporation, Southfield, Mich.

[21] Appl. No.: 189,462

[22] Filed: Sep. 22, 1980

[51] Int. Cl.[3] .............................................. A61M 15/00

[52] U.S. Cl. .............................. 137/81.1; 128/204.26; 128/204.29

[58] Field of Search ...................... 128/204.26, 204.29; 137/81.1, 114

[56] References Cited

U.S. PATENT DOCUMENTS

| | | | |
|---|---|---|---|
| 3,075,957 | 4/1963 | Veit et al. | 137/81.1 |
| 3,077,881 | 2/1963 | Sprague | 137/81.1 |
| 3,179,119 | 4/1965 | Fitt et al. | 137/81.1 |
| 3,474,812 | 10/1969 | Robertson | 137/81.1 X |
| 3,509,895 | 5/1970 | Henneman | 137/81.1 |

FOREIGN PATENT DOCUMENTS

| | | | |
|---|---|---|---|
| 1528734 | 5/1968 | France | 128/204.2 C |

*Primary Examiner*—A. Michael Chambers

*Attorney, Agent, or Firm*—W. G. Christoforo; Bruce L. Lamb

[57] ABSTRACT

An oxygen regulator for controlling the flow of breathing oxygen and uncontaminated air at various altitudes includes a balanced oxygen valve (20) and a balanced air valve (50) which cooperate with a dilution aneroid valve (62) to provide breathable mixture whose oxygen percentage increases with altitude to a predetermined altitude. Above that altitude one hundred percent oxygen is provided. A gas loading aneroid valve (110) operates to increase the oxygen pressure in accordance with altitude over a range of altitude.

7 Claims, 7 Drawing Figures

AUTOMATIC DILUTER/DEMAND OXYGEN REGULATOR ADAPTED FOR CHEMICAL OR BIOLOGICAL USE

This invention relates to apparatus for mixing and controlling the flow of breathing oxygen and uncontaminated air to an aviator before, during and even after flight when there is a possibility of exposure to toxic chemical and biological substances.

An oxygen regulator to be used in a toxic chemical or biological environment to supply a breathable atmosphere to an aviator must meet a number of unusual requirements in addition to mixing diluter air with oxygen. First, it must supply the breathable atmosphere at a slight positive gage pressure in order to exclude the toxic elements in the environment without creating breathing discomfort due to such positive gage pressure. Second, the oxygen regulator must operate over a wide range of altitude from ground level to 50,000 feet or more. More specifically, the oxygen regulator must control an oxygen to diluter air ratio to provide sufficient oxygen partial pressure to prevent hypoxia at low aircraft cabin pressure and sufficient nitrogen partial pressure to prevent atalectisis at cabin pressures where high concentration of oxygen is not necessary to prevent hypoxia. In addition, when delivery of 100% oxygen at ambient pressure does not provide sufficient oxygen partial pressure to prevent hypoxia, oxygen must be delivered under controlled increased pressure. To meet these requirements air for air dilution of the oxygen is delivered under pressure, usually at a pressure of 5 to 10 PSIG, during normal flight. As a result, it is necessary that the oxygen regulator regulate the delivery pressure of two different gases, air and oxygen, in order to control the dilution of oxygen, rather than merely regulating the delivery of ambient air for diluter purposes as in the prior art.

An oxygen regulator built according to the present invention includes two inlet ports, one for receiving pressurized oxygen and the other for receiving a diluter gas for the oxygen such as uncontaminated air. Two balanced valves respectively control the flow of oxygen and diluter gas to an outlet which is adapted to be connected to breathing apparatus such as a face mask or helmet. A diaphragm controls the operation of the balanced oxygen valve. Specifically, outlet pressure is applied to one side of the diaphragm and the gas pressure in a chamber, termed a second chamber in the detailed description to follow, is applied to the other side of the diaphragm. The chamber pressure is controlled by a gas loading valve, which consists of an aneroid valve responsive generally to ambient pressure, and a check valve. The aneroid is ineffective from ground to an ambient pressure corresponding to a predetermined altitude, usually about 30,000 feet. Over this range the check valve is effective to maintain the chamber pressure at about 1.5 inches of water above ambient. At the above mentioned predetermined altitude the aneroid has expanded to move a second check valve into effective operation. The bias spring rate of this second check valve is varied with altitude by the aneroid so that the chamber pressure increases with altitude.

The balanced oxygen valve is designed to be closed when the gas pressure difference across its controlling diaphragm is zero. Thus, there is generally a positive gage pressure at the regulator outlet which increases with altitude. Upon demand at the outlet the outlet pressure drops opening the balanced oxygen valve to admit oxygen into another chamber, termed a first chamber in the following description, which is separated from the outlet by a nozzle or venturi.

The second or balanced air valve also includes a controlling diaphragm which responds to the gas pressure difference between the above mentioned first chamber and a third chamber which receives air from the balanced air valve. The third chamber is separated from the outlet by a dilution aneroid valve which responds to the gas pressure in the third chamber. Like the balanced oxygen valve, the balanced air valve is designed to be closed when the pressure difference across its controlling diaphragm is zero. When the balanced air valve is closed, of course, the third chamber gas pressure is equal to the outlet gas pressure since there is no flow through the dilution valve. However, when demand is made causing the balanced oxygen valve to open, oxygen entering the first chamber deflects the balanced air valve diaphragm causing uncontaminated air to enter the third chamber and flow through the dilution valve to mix with the oxygen stream issuing from the oxygen nozzle. This mixture is available at the outlet.

The dilution aneroid valve is designed to increasingly throttle the flow of dilution air with increasing altitude so that the mixture supplied at the outlet increases in oxygen content until at a certain altitude the dilution aneroid valve closes and pure oxygen is there and at higher altitude provided.

An antisuffocation valve in the form of a tip valve is provided to connect the uncontaminated air inlet port directly to the outlet in the event the oxygen supply fails. The stem of the tip valve is located below the balanced oxygen valve diaphragm. If the oxygen supply fails than no oxygen will enter the first chamber so that the balanced air valve cannot open. Demand will cause a greater suction than normal in this case causing the balanced oxygen valve diaphragm to deflect further than normal to tip the antisuffocation valve stem to supply uncontaminated air through that valve directly to the outlet.

DESCRIPTION OF THE PREFERRED EMBODIMENT

Figure 1:
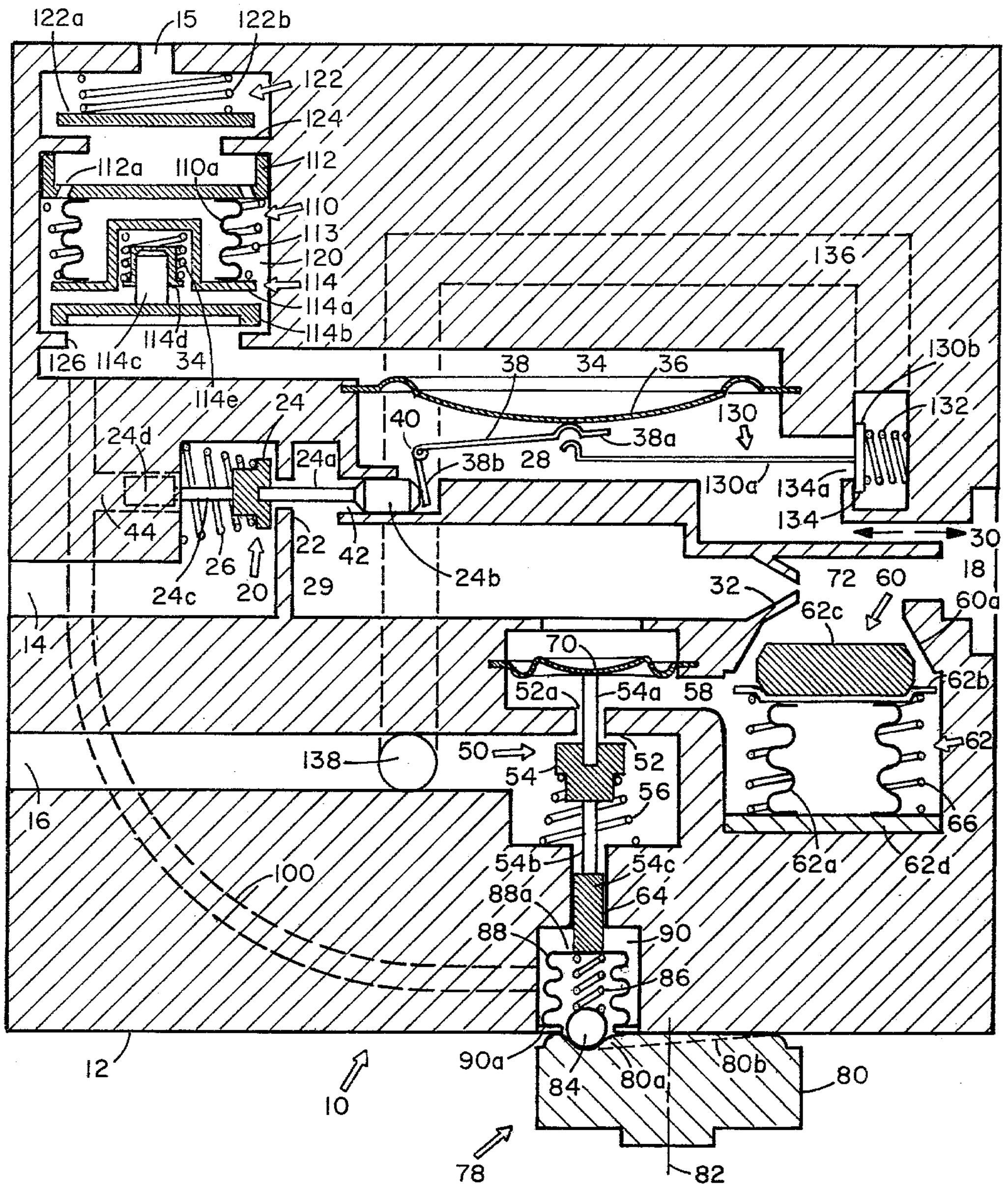
FIG. 1 is a schematic representation of the oxygen regulator of the invention showing the components thereof in position for demand operation at altitudes extending from ground to about 30,000 feet.

Referring to the figures, and particularly to FIG. 1, the oxygen regulator of this invention, indicated generally at 10, is illustrated as consisting of a body 12, a first inlet port 14 normally connected to a supply of oxygen at a predetermined positive gage pressure, a second inlet port 16 normally connected to a supply of uncontaminated air also at a predetermined positive gage pressure, and an outlet 18 normally connected to breathing apparatus such as a helmet or breathing mask of an aircraft pilot or crew member. A balanced oxygen regulator valve 20 consists of a valve seat 22, a valve member 24 and a spring 26 which lightly biases valve member 24 toward valve seat 22. Valve 20 operates to regulate the rate of flow of oxygen from port 14 to outlet 18. More specifically, valve 20 regulates the communication of port 14 with a first chamber 29 which communicates through means such as an oxygen nozzle or venturi 32 to outlet 18. Outlet 18 communicates freely with a volume 28, through the path designated by arrows 30.

Volume 28 is separated from a second chamber 34 by a flexible diaphragm 36 which is displaced in a direction normal to the diaphragm in response to the differential gas pressure between said second chamber and the outlet.

Valve body 24 includes a forwardly extending stem 24*a* with a member 24*b* fitted to slide smoothly in housing bore 42. Valve body 24 also includes a rearwardly extending stem 24*c* having a member 24*d* fitted to slide smoothly in housing bore 44. Member 24*b* bears against the short leg 38*b* of an L-shaped lever crank 38 pivoted on pin 40 which is affixed to housing 12. The long leg 38*a* of lever crank 38 bears generally upon the central portion of diaphragm 36 and is rotated about pin 40 in response to the position thereof. This in turn controls or regulates the lateral position of valve body 24 and hence the communication of inlet port 14 with first chamber 28 through the seat port. It should be noted that spring 26, as mentioned above, lightly biases valve 20 to the closed position so that the valve is closed when the pressures on either side of diaphragm 36 are equal but which opens when the pressure in volume 28 drops slightly with respect to the pressure in second chamber 34.

A balanced air valve 50 consists of a valve seat 52, a valve member 54 and a spring 56 which lightly biases valve member 54 toward valve seat 52. Valve 50 operates to regulate the communication of inlet port 16 with a third chamber 58 which in turn communicates through dilution port 60 with mixing chamber 72. Dilution port 60 is throttled by dilution aneroid valve 62. Valve member 54 includes stem 54*a* which extends forward through valve seat port 52*a* to bear against the underside of diaphragm 70. Valve member 54 also includes a downwardly extending valve stem 54*b* which terminates in member 54*c* which is slidably fitted into housing bore 64 to guide the movement of valve member 54. Flexible diaphragm 70, which separates first chamber 29 from third chamber 58, moves along a line of action normal to its plane surface in response to the gas pressure difference between those chambers.

Dilution aneroid valve 62 which when operated below a predetermined altitude regulates the ratio of uncontaminated air to oxygen in chamber 72, consists of an aneroid capsule 62*a*, which is affixed to housing 12 by plate 62*d*, an elastomer valve member 62*c* which is arranged in cooperation with valve seat 60*a* to throttle dilution port 60 and which is attached to capsule 62*a* through stiffening plate member 62*b*. A spring 66 biases dilution aneroid valve 62 toward the closed condition. Capsule 62*a* is hermetically sealed so that its internal gas pressure is at some predetermined essentially constant value. Thus, as the pressure within chamber 58 drops valve 60 moves toward the closed condition. Of course, so long as valve 60 remains open the gas pressure in chamber 58 is close to and dependent upon the gas pressure at outlet 18. The gas pressure at outlet 18 is in turn close to and dependent upon ambient gas pressure, a difference between the two being the slight positive gage pressure maintained in the aviator's breathing apparatus to exclude the toxic environment as previously explained.

A dilution control means 78 is provided to permit valve 50 to be manually closed so that the oxygen stream is not thereafter diluted. Dilution control means 78 consists of a cam wheel 80 which can be rotated manually about axis 82 and which has an annular ball cam groove 80*a* in its top face. A spring 86 located within flexible bellows 88 and, bearing at one end against bellows end 88*a*, biases a ball 84 into cam groove 80*a*. When cam wheel 80 is rotated about axis 82 ball 84 rides in cam groove 80*a* up along annular ramp 80*b*, thus forcing bellows end 88*a*, through spring 86, against the butt end of member 64 to thus force valve 50 closed to prevent air at port 16 from mixing with the oxygen stream. Bellows 88 is preferably a material which is inert and will not be deteriotated by toxic components of the ambient atmosphere. Bellows 88 includes an end flange 90*a* which is suitably sealed in recess bore 90 to prevent entry of the toxic components into housing 12.

A passageway 100 connects bore 90 with chamber 34, passing by bore 44. Valve stem member 54*c* and bore 64 are sized so that there is normally a slight bleeding of air from port 16 therethrough and through bore 90 and passageway 100 to chamber 34. In like manner valve stem member 24*d* is sized with respect to bore 44 to provide a normal bleeding of oxygen from inlet port 14 therethrough into passageway 100 and to chamber 34. The gas pressure within chamber 34 is controlled by a gas loading aneroid valve 110 supported within a bore 120 by a spider 112 having through holes 112*a* therein. Aneroid valve 110 consists of an aneroid capsule 110*a*, which provides the driving force for the attached valve member 114, which in turn consists of a carrying member 114*a* which is fixedly attached to and carried by capsule 110*a* and a sealing member 114*b* which is resiliently carried by carrying member 114*a* through stem 114*c* and spring 114*e* in central bore 114*d* of carrying member 114. Carrying member 114*a* is biased downward by spring 113.

A safety pressure check valve 122, also contained within bore 120 between aneroid valve 110 and port 15, opens to the ambient environment. Check valve 122 includes valve member 122*a* which is biased toward the closed condition, wherein valve seat 124 is covered, by spring 122*b*. Check valve 122 is designed to open at about 1.5 inches of water above ambient so that there is normally a continuous bleed of gas from chamber 34 to ambient through port 15. This continuous bleed prevents contaminants in the ambient environment from entering through port 15, which is the only opening in the regulator exposed to ambient air.

A second valve seat 126 within bore 120 cooperates with sealing member 114*b* to set the gas pressure within chamber 34 over certain altitude ranges as will be explained below.

An antisuffocation valve in the form of tip valve 130 includes a valve stem 130*a* and valve member 130*b* which is normally held in sealing relation to valve seat 134 by centering spring 132 and the gas pressure in passage 136, which communicates directly with port 16 through port 138. Valve 130 opens to allow air from port 16 to enter outlet 18 through port 138 and passageway 136 when the oxygen supply is interrupted or impeded. In that event suction at outlet 18 due to aviator inhalations will cause diaphragm 36 to deflect enough to tip valve 130. This is designed to occur at a suction of 3.5 to 7 inches of water and is sufficiently noticeable to warn the aviator that he is no longer breathing oxygen.

OPERATION

Figure 5:
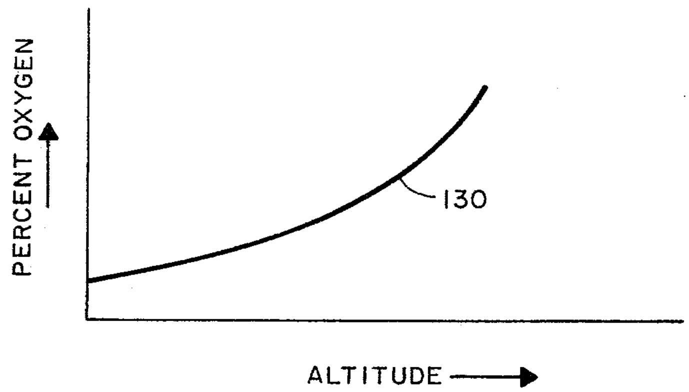
FIG. 5 is a curve of altitude versus oxygen percentage for a typical oxygen regulator built according to the invention.
Figure 6:
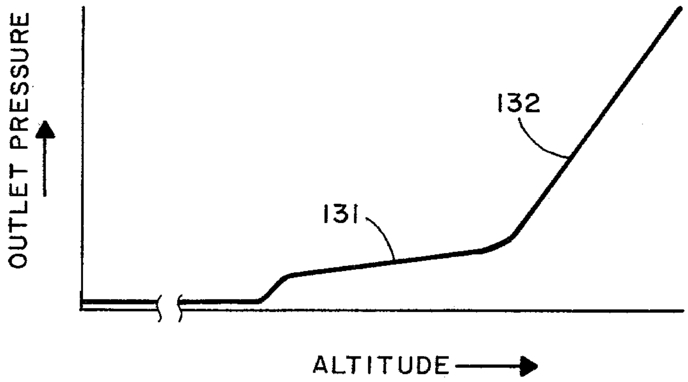
FIG. 6 is a curve of altitude versus outlet pressure for a typical oxygen regulator built according to the invention.

Refer to FIGS. 5 and 6, which are useful in explaining the operational requirements of a typical oxygen regulator built according to the present invention. In particular, FIG. 5 shows that a typical regulator is required to deliver a breathable atmosphere which varies in oxygen content in accordance with curve 130, that is, from about 30% oxygen at sea level to 100% oxygen at 30,000 feet and above. FIG. 6 shows that the same typical regulator is required to provide a breathable atmosphere at a pressure which is only slightly above ambient between ground and 30,000 feet, pressurized somewhat in accordance with slope 131 between 30,000 and 38,000 feet and pressurized in accordance with slope 132 from 38,000 to 50,000 feet.

FIG. 1, reference to which should now again be made, shows the regulator components in the positions they assume during operation between ground and about 30,000 feet altitude. At these altitudes aneroid capsules 110*a* (of gas loading valve 110) and 62*a* (of dilution aneroid valve 62) are relatively compressed. Thus, aneroid valve 110 is open and provides no or negligible loading of the gas pressure within chamber 34. The gas loading in this chamber at the ambient pressures corresponding to the present altitude range is provided by check valve 122, which opens at about 1.5 inches of water above ambient, as previously mentioned. Thus, the gas pressure in chamber 34 is about 1.5 inches of water above the ambient pressure. Upon demand at outlet 18, the resulting suction lowers the outlet pressure and the pressure in volume 28 to about 1.5 inches of water below ambient at which time diaphragm 36 deflects and, operating through lever 38, opens balanced oxygen valve 20 to admit oxygen into first chamber 29 which then flows through nozzle 32 to outlet 18. Of course, the pressure in chamber 29 is somewhat higher than the outlet demand pressure, while the gas pressure in chamber 58 is close to the demand pressure. The resulting pressure imbalance across diaphragm 70 opens the balanced air valve to admit uncontaminated air at port 16 to flow into chamber 58 and through dilution port 60 into mixing chamber 72 where it is mixed with the oxygen flowing from nozzle 32. It will be noticed that due to the balanced nature of valve 50 the gas pressures in chambers 29 and 58 are approximately equal and differ mainly due to the biasing force of spring 56, which is designed to be quite light. Thus, the pressure drop through nozzle 32 is about equal to the pressure drop through dilution port 60 to thus provide better mixing of the air and oxygen in chamber 72. Also note that as to the pressure response of aneroid capsule 62*a*, the gas pressure in chamber 58 is practically equal to the inlet gas pressure, which in turn is very close to ambient pressure, at least over the range of ground to 30,000 feet. Thus, in essence, capsule 62*a* can be said to respond to ambient pressure. Dilution aneroid valve 62 and particularly aneroid capsule 62*a* are designed to cause port 60 to be progressively throttled as altitude increases (ambient pressure decreases) to gradually restrict the passage of dilution air therethrough so that curve 130 of FIG. 5 is followed.

Figure 2:
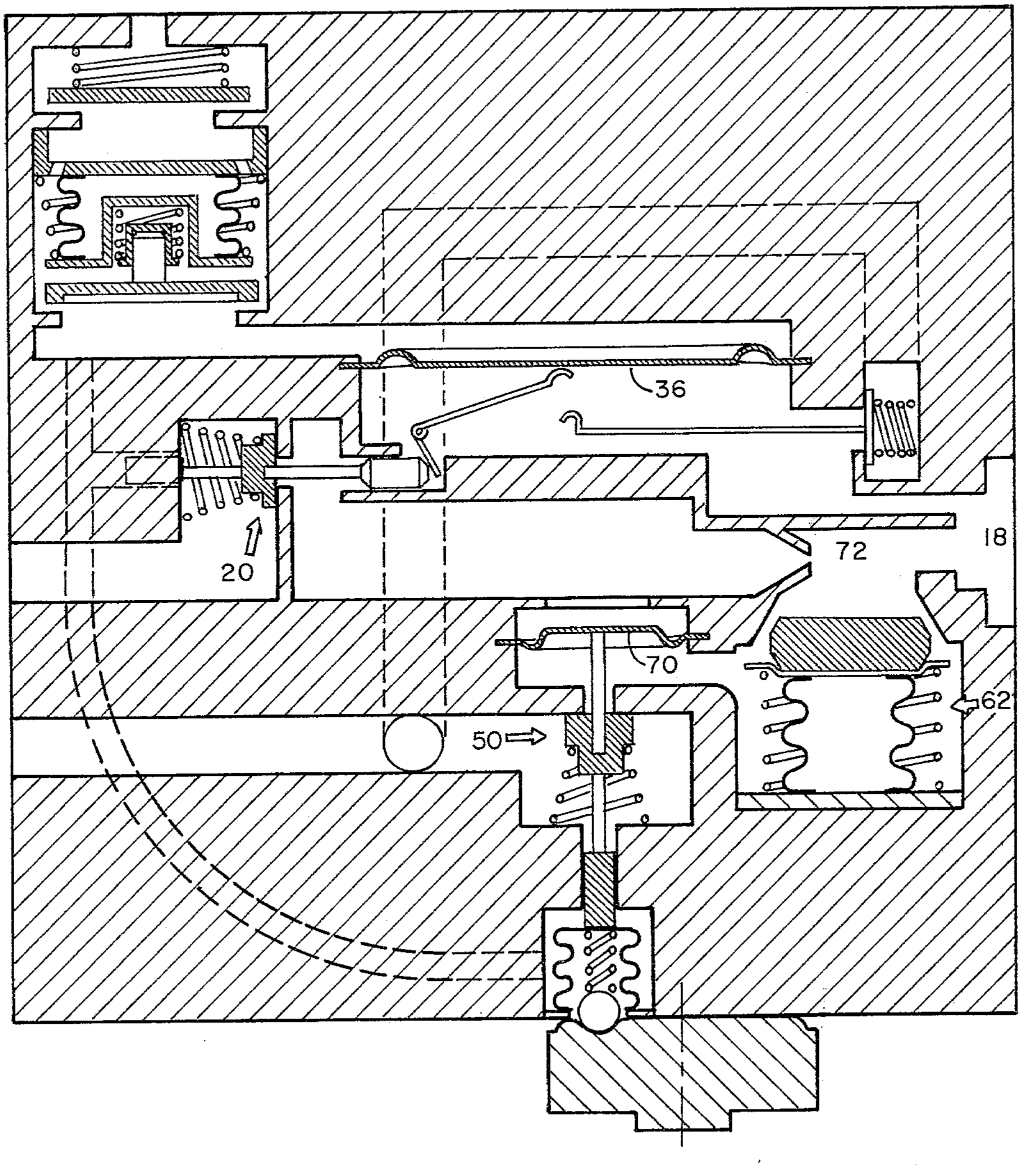
FIG. 2 is a schematic representation similar to that of FIG. 1 with no demand operation from ground level to about 30,000 feet.

FIG. 2, reference to which should now be made, shows the regulator components operating between ground and 30,000 feet with no demand at outlet 18. In this condition diaphragms 36 and 70 are relatively undeflected and balanced valves 20 and 50 are relatively closed. Any opening of these valves at this time would be slight and due primarily to leakage from the aviator's mask or helmet.

Figure 3:
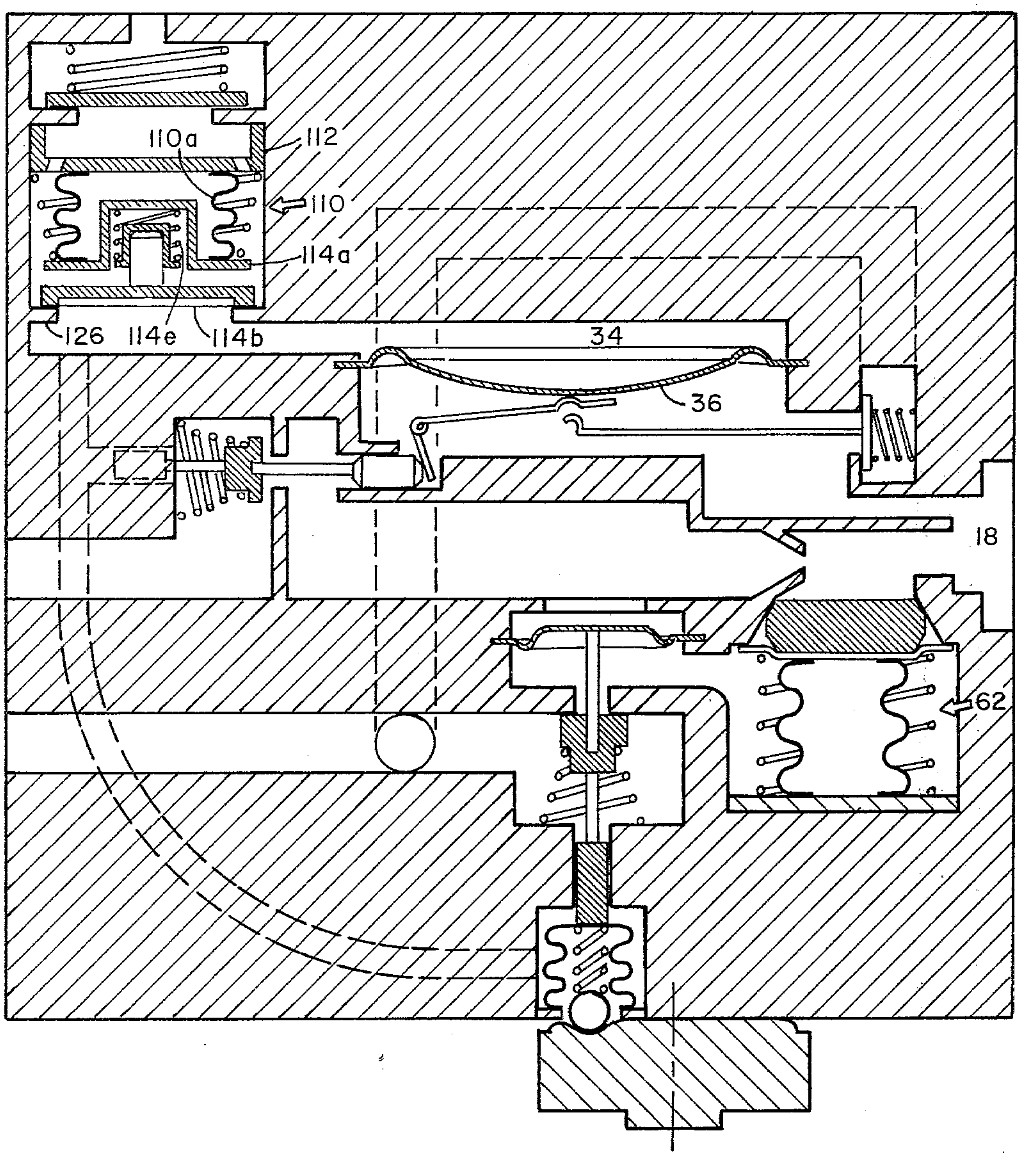
FIG. 3 is a schematic representation similar to that of FIG. 1 with the components in position for demand operation at an altitude range of about 30,000 to about 38,000 feet.

At an ambient pressure corresponding to an altitude of about 30,000 feet dilution aneroid valve 62 closes and thereafter, at higher altitudes, no dilution air is admitted into chamber 72 and only undiluted oxygen is provided at outlet 18. This condition of valve 62 can be seen in FIG. 3 where the regulator components are shown operating at ambient pressure corresponding to an altitude range of about 30,000 to 38,000 feet. At about 30,000 feet, in addition to valve 62 closing, gas loading valve 110 closes, that is, aneroid capsule 110*a* has, at an ambient pressure corresponding to 30,000 feet altitude, expanded so that sealing member 114*b* contacts valve seat 126. Thereafter, as altitude increases from 30,000 to 38,000 feet, sealing member 114*b* and valve seat 126 comprise a check valve which is loaded by spring 114*e*. This increases the gas pressure in chamber 34 so as to bias diaphragm 36 downward. As a result, the outlet pressure required to balance diaphragm 36 must increase a corresponding amount. The outlet pressure increases with altitude along portion 131 of the curve of FIG. 6. Portion 131 slopes upward somewhat illustrating that the gas pressure within chamber 34, and hence the pressure at outlet 18, increases as altitude increases. This is caused by the expansion of aneroid capsule 110*a* with altitude so the loading of spring 114*e* on sealing member 114*b* increases with altitude.

Figure 4:
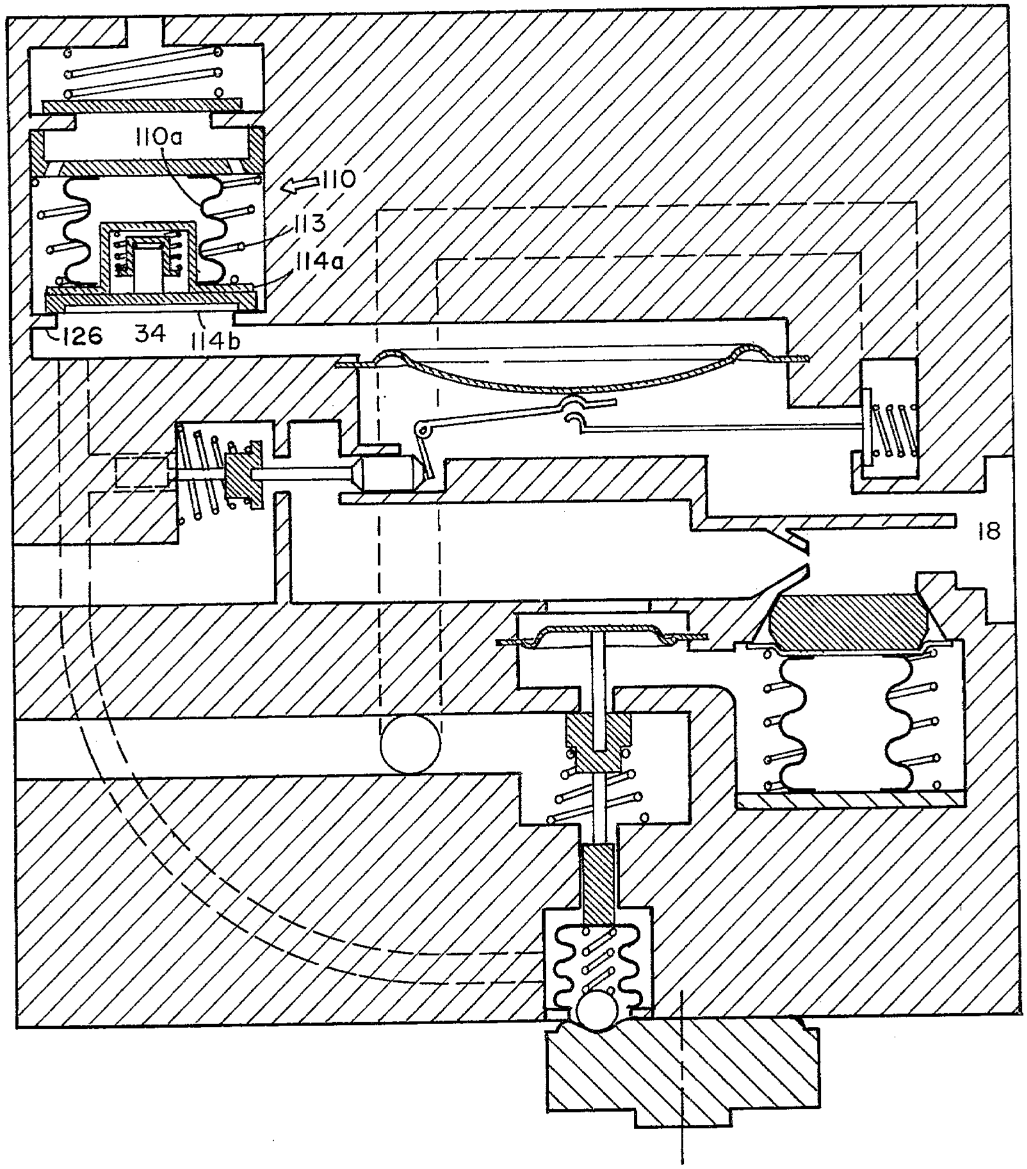
FIG. 4 is a schematic representation similar to that of FIG. 3 with operation at an altitude exceeding about 38,000 feet.

At an ambient pressure corresponding to an altitude of about 38,000 feet aneroid capsule 110*a* has expanded enough to force carrying member 114*a* against sealing member 114*b* as shown in FIG. 4. Thus, at that altitude and higher the check valve comprised of sealing member 114*b* and seat 126 must now work against a bias provided by a spring member comprised of spring 113 and aneroid capsule 110*a*. Above 38,000 feet the bias from spring 113 remains constant but the bias from aneroid capsule 110*a* increases with altitude in accordance with portion 132 of the curve of FIG. 6. Of course, the gas pressure within chamber 34, and hence the regulator outlet pressure, trace the spring bias on valve 110 to provide a pressurized oxygen atmosphere at outlet 18.

Figure 7:
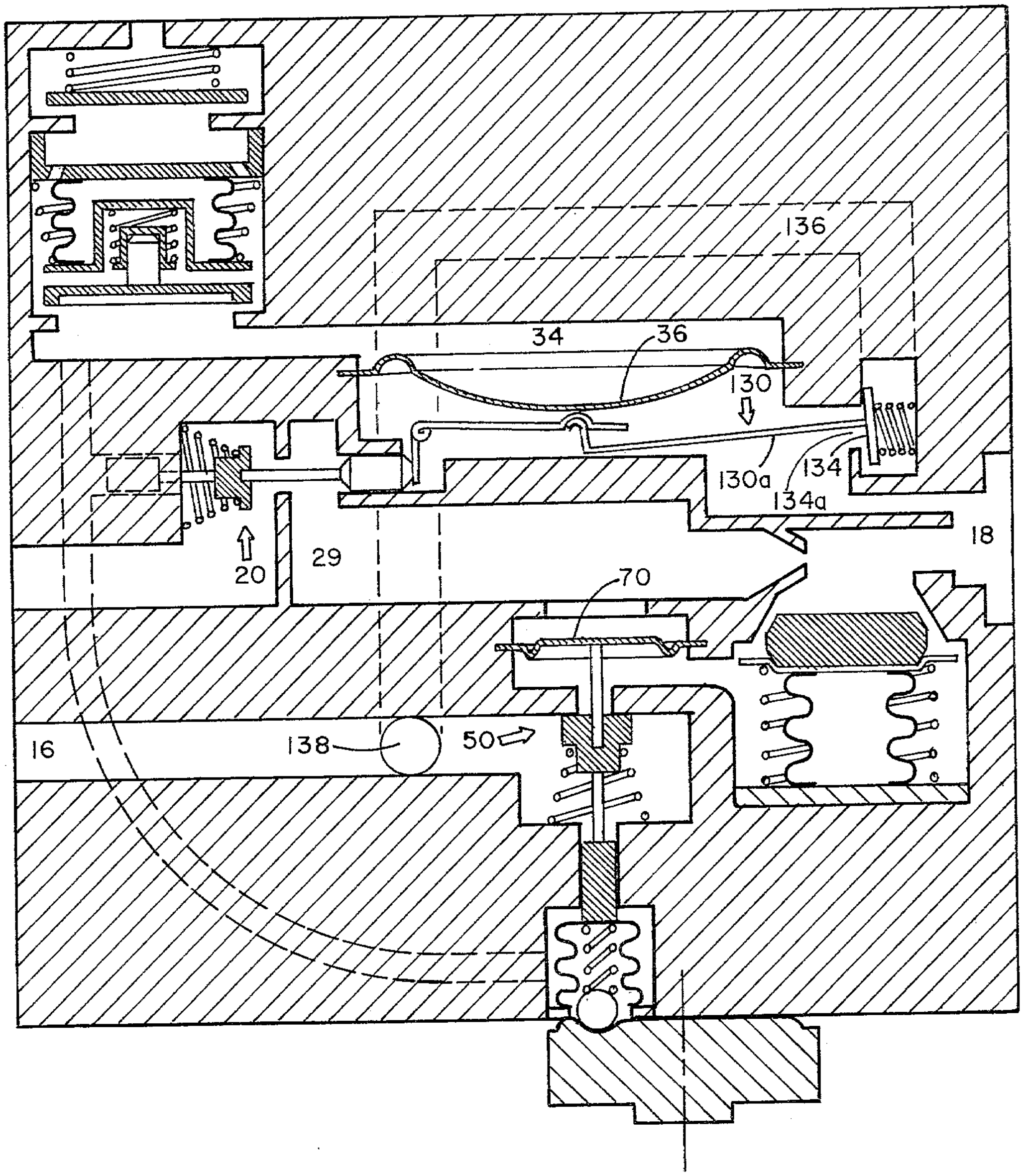
FIG. 7 is a schematic representation similar to that of FIG. 1 illustrating the operation of the antisuffocation valve.

In the event the oxygen supply is interrupted the regulator components will assume the position of FIG. 7, reference to which should now be made. In this situation, since there is no oxygen supply, the pressure within chamber 29 will drop regardless of whether valve 20 is open or closed. This causes diaphragm 70 to be undeflected so that valve 50 closes cutting off the uncontaminated air supply. Demand at outlet 18 will be unsatisfied at the normal 1.5 inches of water below ambient so that suction increases forcing diaphragm 34 to deflect more than usual. At about 5 to 7 inches of water suction at outlet 18 the deflection of diaphragm 36 is enough to topple valve stem 130*a* as shown, opening valve 130 to communicate inlet port 16 to outlet port 18 through port 138, passage 136 and valve seat port 134*a*.

Having described this embodiment of our invention and the operation thereof over a range of altitudes, various modifications and alterations should now present themselves to one skilled in the art. Accordingly, we intend to claim as our property the subject matter covered by the true spirit and scope of the appended claims.

The invention claimed is:

1. An oxygen regulator having a body and comprising in said body:

a first inlet port for pressurized oxygen;

a second inlet port for pressurized diluter gas;

an outlet means adapted to be connected to breathing apparatus;

a first chamber;

a second chamber;

a first balanced valve means responsive to differential gas pressure between said second chamber and said outlet means for regulating the rate of flow of oxygen from said first inlet port to said outlet means via said first chamber;

flow means located between said first chamber and said outlet means for reducing the gas pressure of oxygen flowing therethrough;

a third chamber;

a second balanced valve means located between said second inlet port and said third chamber and responsive to the differential gas pressure between said first and third chambers for regulating the restrictions of said second balanced valve means; and, means responsive to ambient gas pressure for regulating the gas pressure in said second chamber and the communication between said third chamber and said outlet means.

2. The oxygen regulator of claim 1 wherein said flow means comprises a venturi nozzle.

3. The oxygen regulator of claims 1 or 2 wherein said second balanced valve means comprises a flexible diaphragm which separates said first and third chambers and a valve member, valve seat and valve seat port which cooperate with said flexible diaphragm to regulate the restrictions of said valve seat port by said valve member.

4. The oxygen regulator of claim 3 wherein said means responsive to ambient gas pressure includes a first aneroid valve responsive to ambient gas pressure for regulating the pressure in said second chamber and a second aneroid valve responsive to ambient gas pressure for regulating communication between said third chamber and said outlet means.

5. The oxygen regulator of claim 4 wherein said second aneroid valve is sized to close at ambient pressures below about a predetermined ambient pressure whereby communication between said third chamber and said outlet means is interrupted.

6. The oxygen regulator of claim 4 wherein said first aneroid valve comprises a check valve and an aneroid capsule responsive to ambient pressure to urge said check valve into effective arrangement with said second chamber whereby at ambient pressures above a first predetermined pressure said check valve is ineffective to regulate the gas pressure in said second chamber, and at ambient pressures below said first predetermined pressure said check valve effectively regulates the gas pressure in said second chamber.

7. The oxygen regulator of claim 6 wherein said first aneroid valve includes a second check valve effective to regulate the gas pressure in said second chamber at ambient pressure above said first predetermined pressure.

* * * * *